United States Patent [19]

Merritt

[11] 4,026,141
[45] May 31, 1977

[54] METHOD OF AND APPARATUS FOR DETERMINING SURFACE CHARACTERISTICS, SUCH AS COEFFICIENT OF FRICTION, OF A MOVING STRIP OF MATERIAL

[75] Inventor: Robert E. Merritt, Mount Airy, N.C.
[73] Assignee: Renfro Corporation, Mount Airy, N.C.
[22] Filed: Mar. 5, 1976
[21] Appl. No.: 664,094

Related U.S. Application Data

[63] Continuation-in-part of Ser. No. 574,016, May 2, 1975, abandoned.
[52] U.S. Cl. .................................. 73/9; 73/160
[51] Int. Cl.² ................... G01N 19/02; G01L 5/06
[58] Field of Search ............... 73/9, 144, 159, 160

[56] References Cited

UNITED STATES PATENTS

| 2,378,614 | 6/1945  | Zahn          | 73/9   |
| 2,428,379 | 10/1947 | Naumann       | 73/144 |
| 3,526,129 | 9/1970  | Anderson      | 73/144 |
| 3,831,444 | 8/1974  | Sasaki et al. | 73/160 |

FOREIGN PATENTS OR APPLICATIONS

| 842,919 | 7/1960 | United Kingdom | 73/9 |

Primary Examiner—Richard C. Queisser
Assistant Examiner—John S. Appleman
Attorney, Agent, or Firm—Bell, Seltzer, Park & Gibson

[57] ABSTRACT

A method of and apparatus for testing a moving elongate strip of material to determine the coefficient of friction with respect to a control sample having known surface characteristics with a predetermined correlation to the surface characteristics normally encountered by the strip of material in use or processing, and/or the proportion of increased tension caused by movement of the strip in contact with the control sample to the original tension in the strip are provided by this invention. This determination is made by moving the elongate strip of material under tension of any magnitude in sliding frictional engagement with the control sample which moves in response to unbalanced forces generated by the incoming tension and the sliding frictional engagement along a predetermined path of travel, preferably arcuate, until the forces exerted on the control sample become balanced at a given position along the path of travel. The moving strip of material is guided to and from the control sample along respective non-parallel guide paths, with the respective angles of the guide paths changing as the control sample moves along its path of travel until the angles of the respective guide paths become such, with respect to the predetermined path of the control sample, that the forces exerted on the control sample become balanced. The coefficient of friction of the strip of material with respect to the control sample and/or the proportion of increased tension to original tension, are determined and indicated by the position of the control sample along its path of travel when the forces exerted thereon become balanced.

27 Claims, 6 Drawing Figures

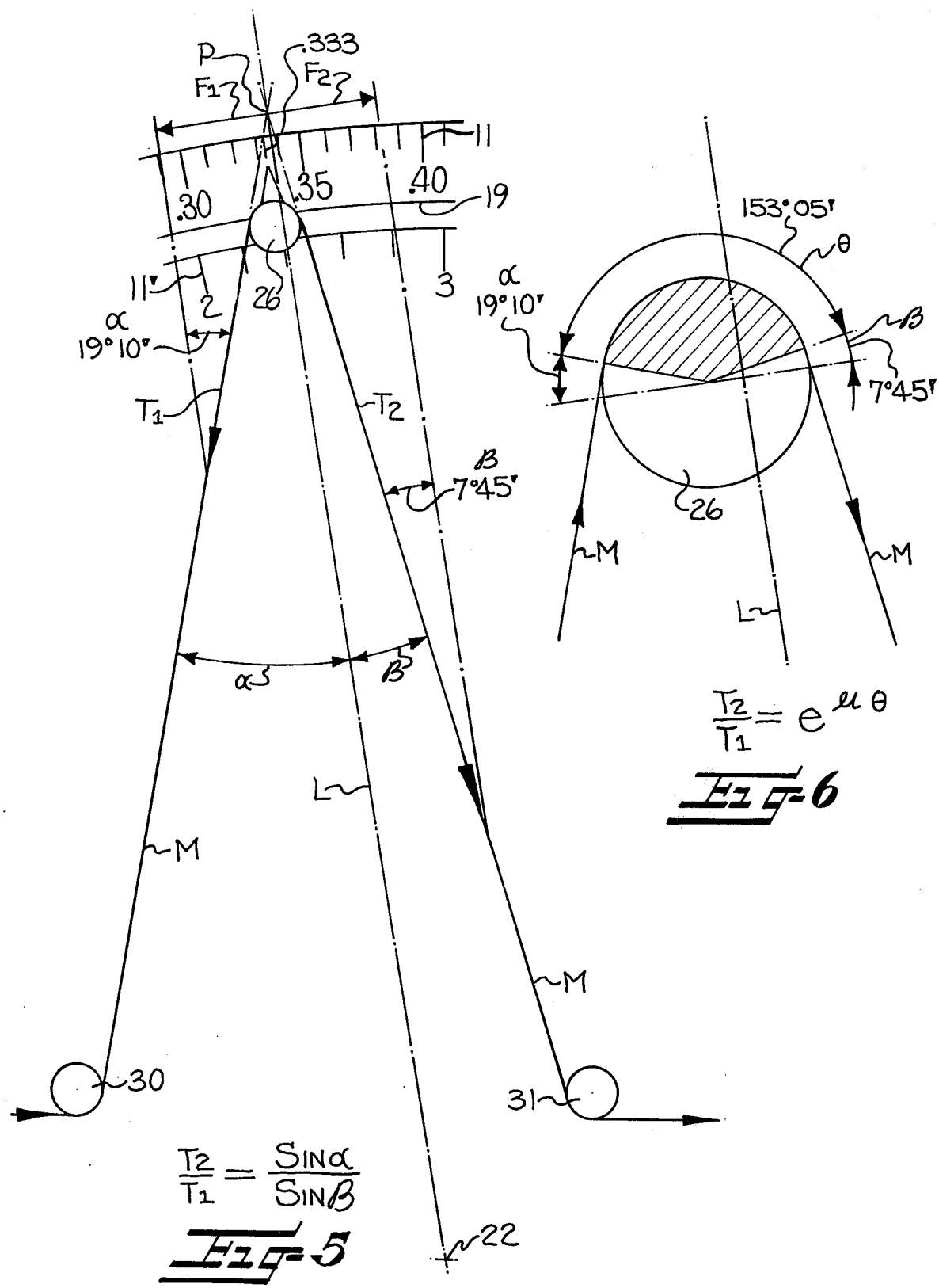

4,026,141

METHOD OF AND APPARATUS FOR DETERMINING SURFACE CHARACTERISTICS, SUCH AS COEFFICIENT OF FRICTION, OF A MOVING STRIP OF MATERIAL

This application is a continuation-in-part of my copending application Ser. No. 574,016, filed May 2, 1975, abandoned, and entitled APPARATUS FOR MEASURING THE COEFFICIENT OF FRICTION OF A MOVING STRIP OF MATERIAL SUCH AS YARNS AND THE LIKE.

This invention relates to a method of and apparatus for testing a moving elongate strip of material under tension to determine certain characteristics thereof with respect to a control sample having known characteristics which are correlated in a predetermined manner to the surface characteristics normally encountered by the strip of material in use or further processing.

BACKGROUND OF THE INVENTION

In use or processing of various types of materials, including yarns, strands, filaments, strips, etc., all collectively hereinafter being referred to for convenience as a "strip of material", there is a definite need for testing the strip of material to determine certain characteristics thereof, such as coefficient of friction or the proportion of increased tension to original tension. One example of a situation in which this need is particularly acute is in the processing of yarns and like strands into fabrics by knitting machines or other like mechanisms. In the knitting of yarns into fabrics, the tension in the various yarns being fed to the needles of the knitting machines is important since the tension in the yarns will affect the size of the knitted product. Therefore, if the tension in the yarns varies significantly from one product to another, the products will vary in size and sizing problems result. This is only one example of the many problems such variance in tension causes in the use or processing of yarns and similar problems are also encountered with other strips of material.

Since the surface characteristics of the strip of material have a marked effect upon the tension therein, an effective device to test strips of material and to determine the surface characteristics thereof with respect to a surface having characteristics correlated to those surface chracteristics normally encountered by the strips of material in use or processing would obviate many, if not all, of the problems caused by variances in tension due to variances in surface characteristics of the strips of material.

Heretofore, no effective devices or methods have been provided for determining the surface characteristics of strips of material with the accuracy and flexibility of use required. Certain testing devices have been proposed for determining the coefficient of friction of a strip of material, but such devices have invariably suffered from the deficiencies of being usable only in a laboratory or test environment which did not permit their use on strips of material actually moving in use or processing; of being excessively large, complicated, expensive and difficult to use; of requiring an accurate control or measurement of incoming tension; of being not self-balancing; or of being so inaccurate as to be available only to a few or do not give the results desired.

SUMMARY OF THE INVENTION

Accordingly, it is the object of this invention to provide a method of and apparatus for testing a moving strip of material under tension of any magnitude to determine the coefficient of friction or other conditions thereof with respect to a control sample having known surface characteristics with a predetermined correlation to the surface characteristics normally encountered by the strip of material in use or processing which determination can be made on strips of material actually moving in use or processing and with a degree of accuracy and ease of operation not heretofore available.

It has been found by this invention that the above object may be accomplished by providing an extremely simple, portable apparatus for testing a moving strip of material, and a method for testing the strip of material utilizing such a portable apparatus, in which a control sample having known surface characteristics with a predetermined correlation to the surface characteristics normally encountered by the strip of material in use or processing is mounted for and moves in a predetermined path of travel when the strip of material is moved in sliding frictional engagement therewith. The strip of material is guided into sliding frictional engagement with the control sample by guide means which are positioned with respect to the control sample so as to guide the strip of material along respective non-parallel guide paths to and from the control sample. The respective angles of these guide paths change with respect to the direction of movement of the control sample as the control sample is moved along its path of travel until the forces exerted on the control sample by the incoming tension and the sliding engagement of the moving strip of material therewith become balanced at a given position along its path of travel. The particular position along the path of travel at which the forces become balanced bears a particular correlation to the surface characteristic defined as the coefficient of friction of the strip of material moving in sliding engagement with the control sample and said coefficient of friction can be determined and indicated with regard to that position of the control sample. Scales are therefore provided which indicate coefficient of friction and the proportion of increased tension to original tension by the position of the control sample along such scales.

Other specific features of this preferred embodiment of this invention will be set forth in the detailed description to follow.

BRIEF DESCRIPTION OF THE DRAWINGS

Some of the objects and advantages of the invention having been stated, other objects and advantages will appear as the description proceeds when taken in conjunction with the accompanying drawings in which:

FIG. 5 is a schematic view illustrating the respective guide paths of the strip of material and the angles of such guide paths and the respective forces being exerted on the control sample in accordance with the method of this invention in the use of the apparatus thereof; and FIG. 6 is an enlarged schematic view of the control sample and illustrating the angle of sliding frictional engagement of the strip of material therewith and the correlation of the respective angles of the guide paths relative to the control sample.

DESCRIPTION OF THE PREFERRED EMBODIMENT

Figure 1:
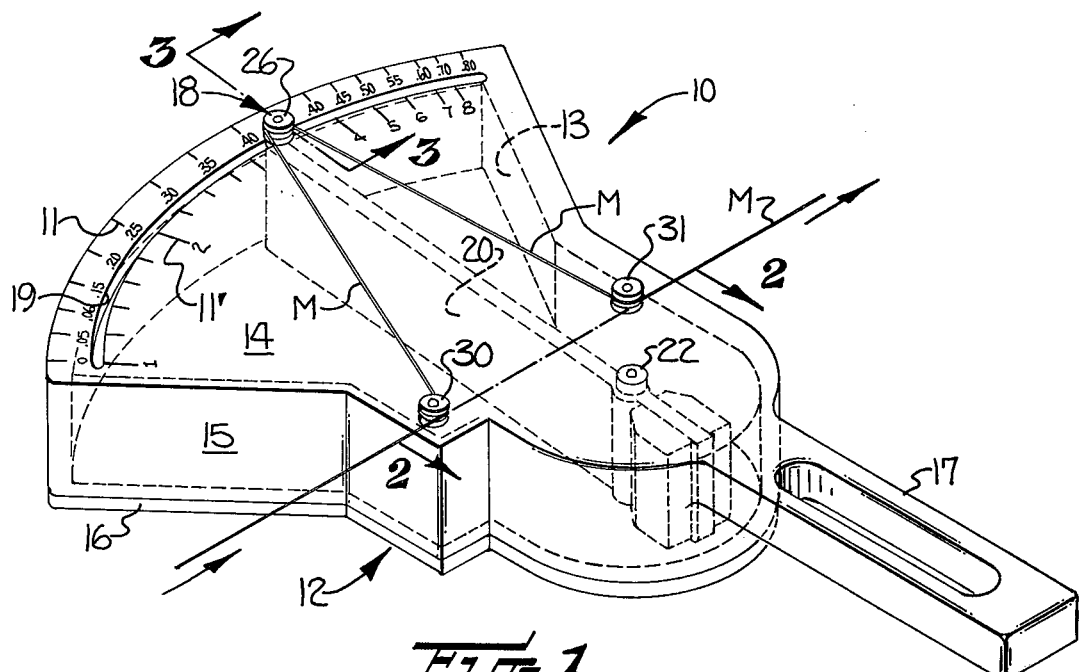
FIG. 1 is a perspective view of the preferred embodiment of the apparatus of this invention.

Referring now to the drawings, a preferred embodiment of apparatus incorporating the features of this invention is illustrated in its entirety in FIG. 1 and generally indicated by the reference numeral 10. Apparatus 10 is in the form of a portable, hand held apparatus having an upper scale 11 containing coefficient of friction values of yarns and the like, and a lower scale 11' containing values of the proportion of increased tension to original tension in the moving strip of material M to indicate thereby the effect of the use of the testing apparatus 10 on the moving strip of material. However, it is to be understood that the novel concepts of this invention could be utilized in other specific constructions and in other environments, such as being mounted in stationary position and forming a part of a particular machine, being utilized for testing other specific materials, or having different scales or indicating systems, such as electronic readouts, in close proximity to the apparatus or remotely mounted.

In the embodiment of the testing apparatus 10 illustrated in the drawings, there is included a portable, generally paddle shaped, housing 12 adapted to be held in the hand of a user and defining a hollow interior 13. The housing 12 includes an outer, upper face 14, side walls 15, a bottom wall 16 removably secured to the side walls 15 and a handle portion 17 for gripping by a user. The hollow interior 13 of the housing 12 is of a predetermined configuration, for purposes to be discussed below. However, while this predetermined configuration of the housing 12 is preferred for this embodiment, it may be desirable to utilize a housing of a different configuration and construction for other uses, particularly when a non-portable apparatus is to be utilized.

Apparatus 10 further includes a control sample 18 having known surface characteristics with a predetermined correlation to the surface characteristics normally encountered by the strip of material M in use or processing. For example, if it is desired to determine the surface characteristics of yarn with respect to steel knitting needles in a knitting machine, the control sample should be of the same type of steel as the knitting needles or of a material having the same or similar surface characteristics. If the strip of material M is to be tested with respect to another material, such as ceramic guides, a control sample 18 having surface characteristics correlated to such other material, e.g. ceramic, should be selected and used.

Figure 4:
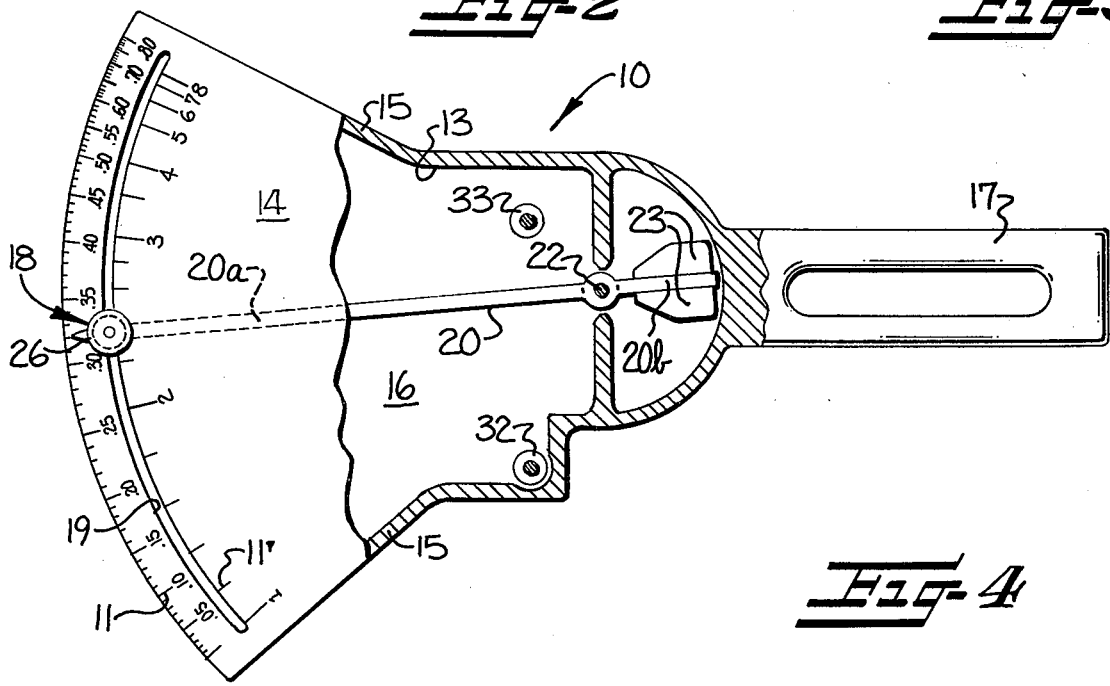
FIG. 4 is a top plan view of the apparatus shown in FIG. 1 with a portion of the top of the apparatus broken away to expose the elements of the apparatus underlying the removed portion of the housing.

Control sample 18 is mounted for movement in a predetermined path of travel and scales 11 and 11' are positioned along that path of travel. While the path of travel of control sample 18 may take many forms within limitations to be described hereinafter, for simplicity it is preferred that this path of travel comprise the arc of a circle. In the disclosed embodiment, the upper face 14 of housing 12 has an arcuate slot 19 formed therein and scales 11 and 11' are mounted along opposite sides of slot 19 (FIGS. 1 and 4). Slot 19 corresponds to the predetermined path of travel of control sample 18.

An elongate lever 20 having opposite outer end portions 20a, 20b is pivotally mounted by a bearing 22 for balanced free oscillating movement in the hollow interior 13 of housng 12 in such a manner that end portion 20a underlies slot 19. Control sample 18 is mounted on the outer end portion 20a of lever 20 in a manner to be presently described. While the preferred location of bearing 22 is intermediate the end portions 20a, 20b of lever 20, other locations from that specifically shown in the drawings may be used.

Preferably, the interior 13 of the housing 12 is generally of a configuration corresponding to the desired oscillating movement of the lever 20, and the lever 20 has a transverse height or dimension along its length substantially equal to the transverse height or dimension of the hollow interior 13 of the housing 12. By this arrangement, an air damping effect will be created by the oscillating movement of the lever 20 within the housing 12 to prevent unwanted rapid and transitory movements of the lever 20.

Preferably, a weight 23 (FIG. 4) is carried on the end portion 20b of the lever 20 for providing a means to counterbalance the lever 20 against the force of gravity so that the lever will be substantially perfectly balanced for free oscillating movement in the event the apparatus 10 is placed in a position other than horizontal.

Figure 3:
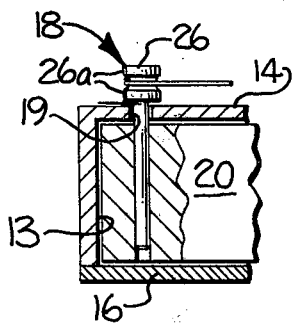
FIG. 3 is a sectional view, taken generally along line 3—3 in FIG. 1.

In the disclosed embodiment, control sample 18 is in the form of a generally cylindrical member 26, but it should be understood that the control sample 18 may be of any desired shape. Cylindrical member 26 is mounted on the end portion 20a of lever 20 and extends upwardly through the slot 19 and outwardly of the outer face 14 of the housing 12 for providing an arcuate surface for receiving the strip of material M in sliding frictional engagement therewith. The cylindrical member 26 preferably includes flanges 26a (FIG. 3) formed around the outside surface thereof for receiving the strip of material M therebetween to prevent the strip from being dislodged from the cylindrical member 26 during its sliding frictional engagement therewith.

Figure 2:
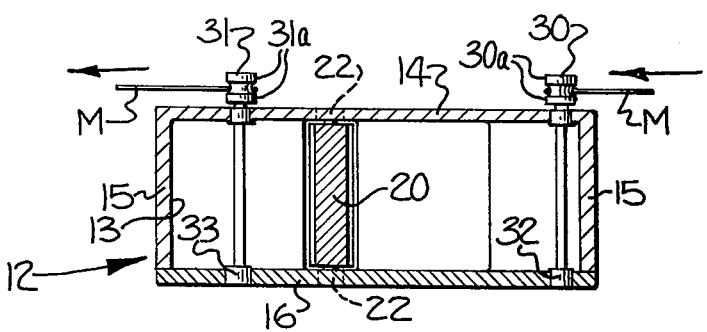
FIG. 2 is a sectional view, taken generally along line 2—2 in FIG. 1.

The apparatus 10 further includes guide means for guiding the moving strip of material M to and from the control sample 18 along respective first and second non-parallel guide paths. As illustrated, these guide means preferably are in the form of generally cylindrical, rotatably mounted, guide members 30 and 31 (FIG. 1) respectively mounted on each side of lever 20 at predetermined positions in relation to control sample 18 and its path of travel defined by slot 19. These guide members 30, 31 may also include flanges 30a, 31a (FIG. 2) around the circumference thereof to receive the strip of material M therebetween and to prevent dislocation of the material M from the guide members 30, 31. The guide members 30, 31 are rotatably mounted on the housing 12 by suitable bearings 32, 33 (FIG. 4) and are freely accessible, as is control sample 18, so that a running length of the strip of material M may be threaded therearound without interrupting movement of the strip of material or the machine to which it is being moved.

The positions of guide members 30 and 31 with respect to control sample 18 and its path of travel are important to the proper operation and calibration of testing apparatus 10. For instance, guide members 30 and 31 should be mounted on opposite sides of a line connecting the center of curvature of the path of travel of control sample 18 with the intersection of extensions of the respective paths of the strip of material M, so that the sliding engagement of the strip of material M with control sample 18 will generate and exert forces on control sample 18 causing the same to move along its path of travel. With such movement of control sample 18 the respective angles of the guide paths of the strip of material between the guide members 30, 31 and the direction of movement of the control sample 18 will change until the forces exerted on control sample 18 become balanced and movement of the control sample ceases.

In the disclosed embodiment, pivot point 22 is located at the center of curvature of the path of travel of control sample 18 and is illustrated as being on the opposite side of a line between the guide members 30 and 31 from control sample 18. It is contemplated by the present invention that the center of curvature of the path of travel could be located at any point along the line or the extension of a line passing through the intersection of the extensions of the respective paths of material M and which lies between the respective paths of the strip of material M. Although the center of curvature could be located at any point along the line just described, different calibrations of scales 11 and 11' will result. There are locations along the line described above, which can be determined by trial and error, which will result in there being more than one point on the path of control sample 18 where the forces reach a balanced condition and a toggle effect would result and the control sample 18 would skip over a portion of its travel when the surface characteristics of the strip of material M changed slightly. While such a toggle effect might be desirable in certain instances, it would not be useful where the coefficient of friction and/or the proportion of increased tension to original tension are to be determined.

The relative positions of guide members 30, 31, control sample 18, and the center of curvature of the path of travel may be chosen to expand or contract portions of scales 11 and 11' to provide more precise readings.

For a better understanding of the method and apparatus of this invention and particularly with respect to the use of the forces generated by the sliding engagement between the strip of material M and control sample 18 and the angles of the respective guide paths to move control sample 18 along its path of travel, the schematic views in FIGS. 5 and 6 may be referred to as illustrating the particular angular relationship of the guide paths and the balancing of the forces exerted on control sample 18. Contrary to most of the previously available test apparatus, there is no necessity with the method and apparatus of accurately controlling or measuring the incoming or original tension $T_1$ in the strip of material M. This method and apparatus will function equally well with an incoming or original tension $T_1$ of any desired magnitude and will do so even if the amount of original tension $T_1$ fluctuates.

Since the sliding engagement between the strip of material M and control 18 results in a frictional drag on the strip of material, the tension $T_2$ in the portion of the strip of material being guided away from control sample 18 will always be greater than the original tension $T_1$ in the portion of the strip of material being guided to control sample 18. Therefore, when the strip of material first moves in sliding engagement with control sample 18, unbalanced forces will be exerted thereon and will cause control sample 18 to move to a position wherein the respective angles of the guide paths become such, with respect to the path of travel, that the forces exerted on control sample 18 become balanced. In FIGS. 5 and 6 there is illustrated a condition wherein control sample 18 has moved to a position wherein these forces have become balanced.

The forces acting on control sample 18 may be considered as acting at a point P corresponding to the intersection of extensions of the respective guide paths along which the strip of material is guided. The respective angles of the guide paths are established or defined between the guide paths and a line L drawn between the pivot point 22 and the point P. As illustrated, the first guide path establishes or defines an included angle $\alpha$ with respect to this line L, while the second guide path establishes or defines an angle $\beta$ with respect to this line L. To effect movement of control sample 18 along its path of travel, the angle between the first and second guide paths, i.e. angle $\alpha$ plus angle $\beta$, should be more than zero but less than 180°.

By vector analysis, illustrated in FIG. 5, the forces acting on control sample 18 have been separated into components and the components effecting movement of control sample 18 are referred to as $F_1$ and $F_2$. The force vector components $F_1$ and $F_2$ are drawn at right angles to the line L at point P and are equal and opposite. The length of force vectors $F_1$ and $F_2$ may be determined as follows:

$$F_1 = T_1 \sin \alpha$$

$$F_2 = T_2 \sin \beta$$

When a balanced condition is reached, as is shown in FIG. 5, the proportion of increased tension $T_2$ to original tension $T_1$ may be expressed as:

$$T_2/T_1 = \sin \alpha / \sin \beta$$

It is well known that the coefficient of friction of a moving strip or belt over a cylindrical member may be defined by the relationship:

$$T_2/T_1 = e^{\mu\theta}$$

In this relationship, $e$ is the Napierian logarithmic base of 2.718..., $\mu$ is the coefficient of friction and $\theta$ is the angle of wrap of the strip of material around the cylindrical member in radians. In the arrangement illustrated in FIGS. 5 and 6, the angle of wrap $\theta$ may be determined as follows:

$$\theta = \pi/180° \, (180° - \alpha - \beta)$$

Thus the value of $T_2/T_1$, determined in the manner previously described, may be substituted into the above relationship for determining the value of the coefficient of friction $\mu$ at any given position of the control sample 18.

By way of example, in the relative positions of the components illustrated in FIGS. 5 and 6, the angle $\alpha$ equals 19° 10' and the angle $\beta$ equals 7° 45'. Thus, the value of $T_2/T_1$ may be determined as follows:

$$T_2/T_1 = \sin \alpha / \sin \beta$$

$$T_2/T_1 = \sin 19°10' / \sin 7° 45'$$

$$T_2/T_1 = 0.32832/0.13485$$

$T_2/T_1 = 2.4347$

The value of the angle of wrap $\theta$ may be determined by:

$\theta = \pi/180° (180° - \alpha - \beta)$ $\theta = \pi/180° (180° - 19° 10' - 7° 45')$ $\theta = \pi/180° (153° 05') = \pi/180° (153.0833°)$ $\theta = 153.083°/57.29577°$ $\theta = 2.6718$ radians Having thus determined the value of $T_2/T_1$ and the value of the angle of wrap $\theta$ in radians, these values may be inserted into the relationship:

$T_2/T_1 = e$ $2.4347 = e^{2.6718}$ $2.6718\mu = LN2.4347$ $2.6718\mu = 0.8898$ $\mu = 0.8898/2.6718$ $\mu = 0.333$

By similar calculations, coefficients of friction can be determined for all positions of control sample 18 along its path of travel as is illustrated by scale 11. In describing the present method and apparatus, the thickness of the strip of material M has been regarded as insignificant with respect to the dimension of apparatus 10 and the relationship described. However, if the thickness of the strip becomes great enough to affect significantly the calibration of the apparatus, this additional factor may readily be taken into account in a manner well known to those skilled in the art.

Up to this point the present method and apparatus have been described with respect to determining the coefficient of friction of the strip at a given location along its length by an indication on the scale 11 once the forces become balanced and movement of the control sample ceases. It should be understood that the coefficient of friction of the strip of material being tested will most likely vary along its length and the control sample 18 will move back and forth along its path of travel as the surface characteristics of the strip vary. It is contemplated by this invention that the degree of change in the coefficient of friction along the length of the strip being tested may be determined by the frequency and amplitude of movement of control sample 18 along its path of travel.

Thus, this invention has provided a novel method of and apparatus for testing a moving strip of material to determine the coefficient of friction, with respect to a control sample having known surface characteristics with a predetermined correlation to the surface characteristics normally encountered by the strip of material in use or processing, and the degree of changes thereof along the strip being tested. In addition, the proportion of increased tension to original tension may also be determined. The method of the instant invention has been described with specific reference to apparatus 10, but it should be understood that the instant method contemplates the use of any apparatus capable of performing the steps thereof.

In the drawings and specification, there has been set forth a preferred embodiment of the invention, and although specific terms are employed, they are used in a generic and descriptive sense only and not for purposes of limitation.

That which is claimed is:

1. A method of testing a moving elongate strip of material to determine certain surface characteristics, such as the coefficient of friction, thereof with respect to a control sample having known surface characteristics, said method comprising the steps of:

selecting a control sample having known surface characteristics;

moving the strip of material under tension over the surface of the control sample in sliding engagement therewith while guiding the strip of material to and from the surface of the control sample along respective non-parallel guide paths; and while causing the control sample to move along a predetermined path of travel and thereby changing the respective angles of said guide paths until said angles become such, with respect to the predetermined path of travel of the control sample, that the forces exerted on the control sample become balanced; and determining the coefficient of friction of the strip of material by the location of the control sample along its predetermined path of travel.

2. A method according to claim 1 wherein the proportion of increased tension in the strip of material resulting from the sliding engagement of the moving strip of material with the surface of the control sample to the tension in the strip of material prior to such sliding engagement is determined.

3. A method according to claim 1 wherein said control sample is caused to move along an arcuate path of travel.

4. A method of testing a moving elongate strip of material comprising the steps of:

selecting a control sample having known surface characteristics;

moving the strip of material under tension over the surface of the control sample in sliding engagement therewith while guiding the strip of material to and from the surface of the control sample along respective non-parallel guide paths; and while causing the control sample to move along a predetermined arcuate path of travel and thereby changing the respective angles of said guide paths until said angles become such, with respect to the predetermined path of travel of the control sample, that the forces exerted on the control sample become balanced; and determining at least one of (a) the coefficient of friction of the strip of material and (b) the proportion of increased tension to original tension in the strip of material by the location of the control sample along its predetermined path of travel.

5. A method according to claim 4 wherein the control sample is caused to move along an arcuate path of travel having a substantially uniform radius of curvature.

6. A method of testing a moving elongate strip of material comprising the steps of:

selecting a control sample having surface characteristics with a predetermined correlation to the surface characteristics normally encountered by the strip of material in use or processing;

moving the strip of material under tension over the surface of the control sample in sliding engagement therewith while guiding the strip of material to and from the surface of the control sample along respective first and second non-parallel guide paths; and while causing the control sample to move along a predetermined arcuate path of travel and thereby changing the respective angles of said guide paths until said angles become such, with respect to the path of travel of the control sample, that the force exerted on the control sample become balanced; and determining at least one of (a) the coefficient of friction of the strip of material and (b) the proportion of the increased tension to original tension in the strip of material prior to such engagement by the location of the control sample along its predetermined path of travel.

7. A method according to claim 6 wherein the proportion of tensions is determined by the relationship $\sin \alpha / \sin \beta$, where $\alpha$ is the angle between said first guide path and a line drawn between the center of curvature of said arcuate path of travel and the intersection of extensions of said guide paths and $\beta$ is the angle between said second guide path and that same line.

8. A method according to claim 6 wherein the coefficient of friction is determined by the equation $\sin \alpha / \sin \beta = e$, where $\alpha$ is the angle between said first guide path and a line drawn between the center of curvature of said arcuate path of travel and the intersection of extensions of said guide paths, $\beta$ is the angle between said second guide path and that same line, $e$ is the Napierian logarithmic base of 2.718, $\mu$ is the coefficient of friction, and $\theta$ is the difference in radians between $\pi$ and $\alpha + \beta$.

9. A method of testing a moving elongate strip of material to determine changes in the coefficient of friction thereof with respect to a control sample having known surface characteristics, said method comprising the steps of:

selecting a control sample having known surface characteristics;

moving the strip of material under tension over the surface of the control sample in slidig engagement therewith while guiding the strip of material to and from the surface of the control sample along respective non-parallel guide paths; and while causing the control sample to move along a predetermined path of travel in response to forces exerted on the control sample by reason of the sliding engagement of the strip therewith, which forces vary as the coefficient of friction of the strip varies; and determining the changes in the coefficient of friction of the strip of material along its length by the amplitude of movement of the control sample along its predetermined path of travel.

10. Apparatus for testing a moving elongate tensioned strip of material to determine certain surface characteristics, such as coefficient of friction, thereof with respect to a control sample having known surface characteristics, said apparatus comprising:

means mounting said control sample for sliding frictional engagement of the moving strip of material therewith and for movement in a predetermined path of travel in response to the exertion thereon of unbalanced forces generated by the sliding engagement of the moving strip of material with said control sample;

guide means mounted at predetermined positions in relation to said control sample for guiding the moving strip of material to and from said control sample along respective non-parallel guide paths, so that forces generated by the sliding engagement of the moving strip of material with said control sample will be exerted on said control sample and will cause said control sample to move along its path of travel until the respective angles of said guide paths become such, with respect to the predetermined path of travel of the control sample, that the forces exerted on said control sample become balanced and movement thereof ceases; and means operatively associated with said predetermined path of travel for indicating the coefficient of friction of the strip of material determined by the position of said control sample along said path of travel.

11. Apparatus according to claim 10 wherein said indicating means also indicates the proportion of increased tension to original tension in the strip of material.

12. Apparatus according to claim 10 wherein said mounting means mounts said control sample for movement along an arcuate path of travel.

13. Apparatus for testing a moving elongate tensioned strip of material with respect to a control sample having known surface characteristics, said apparatus comprising means mounting said control sample for sliding frictional engagement of the moving strip of material therewith and for movement along a predetermined arcuate path of travel in response to the exertion thereon of forces generated by the sliding engagement of the moving strip of material with said control sample;

guide means mounted on opposite sides of said control sample at predetermined positions in relation to said control sample for guiding the moving strip of material to and from said control sample along respective non-parallel guide paths, so that forces generated by the sliding engagement of the moving strip of material with said control sample will be exerted on said control sample and will cause said control sample to move along its path of travel until the respective angles of said guide paths become such, with respect to the predetermined arcuate path of travel of the control sample, that the forces exerted on said control sample become balanced and movement thereof ceases; and means operatively associated with said predetermined arcuate path of travel for indicating at least one of (a) the coefficient of friction of the moving strip of material and (b) the proportion of increased tension to original tension in the strip of material.

14. Apparatus according to claim 13 wherein said mounting means mounts said control sample for movement along an arcuate path of travel having a substantially uniform radius of curvature.

15. Apparatus for testing a moving elongate tensioned strip of material with respect to a control sample having known surface characteristics with a predetermined correlation to the surface characteristics normally encountered by the strip of material in use or processing, said apparatus comprising:
  means mounting said control sample for sliding frictional engagement of the moving strip of material therewith and for movement along a predetermined arcuate path of travel having a substantially uniform radius of curvature in response to the exertion thereon of forces generated by the sliding engagement of the moving strip of material with said control sample;
  guide means mounted on opposite sides of said control sample and between said control sample and the center of curvature of its arcuate path of travel for guiding the moving strip of material to and from said control sample along respective non-parallel first and second guide paths, so that forces generated by the sliding engagement of the moving strip of material with said control sample will be exerted on said control sample and will cause said control sample to move along its path of travel until the respective angles of said guide paths become such, with respect to the predetermined path of travel of the control sample, that the forces exerted on said control sample become balanced and movement thereof ceases;
  means operatively associated with said predetermined arcuate path of travel for indicating at least one of (a) the coefficient of friction of the moving strip of material and (b) the proportion of increased tension to original tension in the strip of material.

16. Apparatus according to claim 15 wherein said mounting means defines an arcuate slot and mounts said control sample for movement along said arcuate slot.

17. Apparatus according to claim 16 wherein said mounting means includes a pivotally mounted lever having its pivot point at the center of curvature of said arcuate slot and one end portion thereof underlying said arcuate slot and mounting said control sample.

18. Apparatus according to claim 16 wherein said indicating means comprises scale means mounted along said arcuate slot and including indicia calibrated to the positions of said control sample along said slot to indicate at least one of (a) coefficient of friction of the strip of material and (b) the proportion of increased tension to original tension in the strip of material by the position of said control sample along said slot.

19. Apparatus for testing a moving elongate tensioned strip of material to determine changes in the coefficient of friction thereof with respect to a control sample having known characteristics, said apparatus comprising:
  means mounting said control sample for sliding frictional engagement of the moving strip of material therewith and for movement along a predetermined path of travel in response to the exertion thereon of forces generated by the sliding engagement of the moving strip of material with said control sample;
  guide means mounted at predetermined positions in relation to said control sample and its predetermined path of travel for guiding the moving strip of material to and from said control sample along respective non-parallel guide paths, so that forces generated by the sliding engagement of the moving strip of material with said control sample will be exerted on said control sample and will cause said control sample to move along its path of travel, and
  means operatively associated with said path of travel for indicating changes in the coefficient of friction of the strip of material along its length by the amplitude of movement of the control sample along its path of travel.

20. Apparatus for testing a moving elongate tensioned strip of material to determine certain surface characteristics thereof with respect to a control sample having known surface characteristics with a predetermined correlation to the surface characteristics normally encountered by the strip of material in use or processing, said apparatus comprising:
  an elongate lever including means pivotally mounting said lever for balanced free oscillating movement;
  a generally cylindrical control sample on said lever for receiving the strip in sliding frictional engagement therearound at an included angle of wrap of $\theta$ to create oppositely directed forces on said lever which resolve or balance themselves at a given position in the oscillating movement of said lever, thereby rendering said lever substantially stationary during continued movement of the strip;
  guide means mounted on each side of said lever at predetermined fixed positions in relation thereto for guiding the moving tensioned strip to and from said control sample in guide paths establishing respective acute included angles $\alpha$ and $\beta$ with respect to said lever; and
  means operatively associated with said lever for indicating coefficient of friction values in relation to the position of said lever when the frictional forces become balanced and determined by a relationship of $\sin \alpha / \sin \beta = e^{\mu\theta}$, for which $\mu$ is the coefficient of friction, $e$ is the Napierian logarithmic base of 2.718 ... and $\theta$ is the difference in radians between $\pi$ and $\alpha + \beta$.

21. Apparatus, as set forth in claim 20, in which said means for indicating coefficient of friction values comprises scale means disposed along an arc of a circle formed by a radius extending from said means pivotally mounting said lever and positioned adjacent the oscillating path of movement of said lever and having coefficient of friction identifying indicia thereon of values determined in accordance with the relationship of said included angles $\alpha$, $\beta$ and $\theta$ and the relative position of said lever when the forces become balanced.

22. Apparatus for testing a moving elongate tensioned strip of material to determine certain surface characteristics thereof with respect to a control sample having known surface characteristics with a predetermined correlation to the surface characteristics normally encountered by the strip of material in use or processing, said apparatus comprising:
  a housing defining a hollow interior of predetermined configuration and having an outer face on one side thereof;
  an elongate lever including bearing means carried by said housing for pivotally mounting said lever within said hollow interior of said housing for balanced free oscillating movement thereof in an arcuate path determined by the configuration of said housing;

a slot formed in said outer face of said housing and disposed along an arc of a circle formed by a radius extending from said means pivotally mounting said lever;

a generally cylindrical control sample mounted on said lever and extending upwardly through said slot and outwardly of said outer face of said housing for oscillating movement with said lever along said slot for receiving the strip in sliding frictional engagement to create oppositely directed forces on said lever which resolve or balance themselves at a given position in the oscillating movement of said lever, thereby rendering said lever substantially stationary during continued movement of the strip;

rotatably mounted, generally cylindrical guide members mounted on each side of said lever generally in a zone between said bearing means and said control sample and being spaced predetermined unequal distances from said lever; and means operatively associated with said lever for indicating at least one of (a) coefficient of friction of the strip and (b) proportion of increased tension to original tension in relation to the position of said lever when the forces become balanced and in a range of values determined by the positions of said guide members.

23. Apparatus, as set forth in claim 22, in which said indicating means comprises scale means disposed along said slot and having coefficient of friction and/or proportion of increased tension to original tension identifying indicia thereon for being indicated by the position of said cylindrical member along said scale means.

24. Apparatus, as defined in claim 22, in which said control sample mounted on said lever includes means for removably mounting said control sample for replacement by other control samples of other predetermined materials.

25. Apparatus, as set forth in claim 22, in which said lever includes a transverse height substantially equal to the transverse height of said hollow interior of said housing for creating an air damping during the oscillating movement of said lever.

26. Apparatus, as set forth in claim 22, in which said apparatus further includes means on said lever for counterbalancing said lever against the force of gravity so that said lever will be balanced in the event it is placed in a position other than horizontal.

27. Apparatus for testing a moving elongate tensioned strip of material to determine certain surface characteristics thereof with respect to a control sample having known surface characteristics with a predetermined correlation to the surface characteristics normally encountered by the strip of material in use or processing, said apparatus comprising:

a portable housing adapted to be held in the hand of a user and defining a hollow interior of predetermined configuration and having an outer face on one side thereof;

an elongate lever including bearing means carried by said housing for pivotally mounting said lever within said hollow interior of said housing for balanced free oscillating movement thereof in an arcuate path determined by the configuration of said housing;

means on said lever for counterbalancing said lever against the force of gravity so that said lever will be balanced in the event it is placed in a position other than horizontal;

a slot formed in said outer face of said housing and disposed along an arc of a circle formed by a radius extending from said means pivotally mounting said lever;

a generally cylindrical control sample mounted on said lever and extending upwardly through said slot and outwardly of said outer face of said housing for oscillating movement with said lever along said slot for receiving the strip in sliding frictional engagement therearound at an included angle of wrap of $\theta$ to create oppositely directed forces on said lever which resolve or balance themselves at a given position in the oscillating movement of said lever, thereby rendering said lever substantially stationary during continued movement of the strip;

rotatably mounted, generally cylindrical, guide members mounted on each side of said lever generally in a zone between said bearing means and said control sample and being spaced predetermined unequal distances from said lever for guiding the moving tensioned strip to and from said control sample in guide paths establishing respective acute included angles $\alpha$ and $\beta$ with respect to said lever; and scale means disposed along said slot and having coefficient of friction and proportion of increased tension to original tension identifying indicia thereon of values each determined in relation to the position of said lever adjacent thereto when the forces become balanced and by respective relationships of $\sin \alpha / \sin \beta = e^{\mu\theta}$, for which $\mu$ is the coefficient of friction, $e$ is the Napierian logarithmic base of 2.718... and $\theta$ is the difference in radians between 180° and $\alpha + \beta$, and of $T_2/T_1 = \sin \alpha / \sin \beta$.

* * * * *

UNITED STATES PATENT AND TRADEMARK OFFICE
CERTIFICATE OF CORRECTION

PATENT NO. : 4,026,141
DATED : May 31, 1977
INVENTOR(S) : Robert E. Merritt

It is certified that error appears in the above-identified patent and that said Letters Patent are hereby corrected as shown below:

Column 5, line 62, after "control" insert --sample--.

Column 6, line 44, "$T_2/T_1 = e$" should be --$T_2/T_1 = e^{\mu\theta}$--.

Column 7, line 20, "$T_2/T_1 = e$" should be --$T_2/T_1 = e^{\mu\theta}$--.

Column 7, line 22, "$2.4347 = e^{2.6718}$" should be --$2.4347 = e^{2.6718\mu}$--.

Column 9, line 15, "force" should be --forces--.

Column 9, line 33, "$\beta = e$" should be --$\beta = e^{\mu\theta}$--.

Column 9, line 49, "slidig" should be --sliding--.

Column 12, line 38, "$\alpha/\sin \beta = e$" should be --$\alpha/\sin \beta = e^{\mu\theta}$--.

Column 14, line 47, "$\alpha/\sin \beta = e$" should be --$\alpha/\sin \beta = e^{\mu\theta}$--.

Signed and Sealed this thirtieth Day of August 1977

[SEAL]

Attest:

RUTH C. MASON
Attesting Officer

C. MARSHALL DANN
Commissioner of Patents and Trademark